United States Patent [19]

Bodenmüller et al.

[11] Patent Number: 5,288,614
[45] Date of Patent: Feb. 22, 1994

[54] METHOD FOR THE DETECTION OF MALIGNANT DISEASES

[75] Inventors: Heinz Bodenmüller; Andreas Dessauer, both of Tutzing, Fed. Rep. of Germany

[73] Assignee: Boehringer Mannheim GmbH, Mannheim, Fed. Rep. of Germany

[21] Appl. No.: 730,953

[22] PCT Filed: Dec. 27, 1990

[86] PCT No.: PCT/SE90/02314
§ 371 Date: Jul. 23, 1991
§ 102(e) Date: Jul. 23, 1991

[87] PCT Pub. No.: WO91/10139
PCT Pub. Date: Jul. 11, 1991

[30] Foreign Application Priority Data

Dec. 27, 1989 [DE] Fed. Rep. of Germany ....... 3942999

[51] Int. Cl.$^5$ .................. G01N 33/574; C12N 15/06; C07K 15/28
[52] U.S. Cl. .................... 435/7.23; 435/7.5; 435/7.94; 435/240.27; 436/64; 530/388.85; 530/391.1; 530/391.3; 530/828
[58] Field of Search ............. 435/7.23, 7.92, 7.94, 435/7.5, 240.27; 436/64; 530/388.8, 388.85, 391.1, 391.3, 828, 324, 326, 327

[56] References Cited

U.S. PATENT DOCUMENTS 4,727,021 2/1988 Cote et al. ................ 435/7.23
4,775,620 10/1988 Cardiff et al. .............. 435/7.23

OTHER PUBLICATIONS

Stasiak et al, J. Invest. Dermatol., 92(5):707–716 (May 1989).
Wiedmann et al, Gastroenterology 96 (5 Part 2) A673 (May 1989).
Karsten et al, Eur. J. Cancer Clin. Oncol., 21:6 733–740 (1985).
Lerner, Nature, 299:592–596 (Oct. 14, 1982).
Suter et al, Immunology Letters, 13:313–316 (1986).
Sundström et al, J. Histochem. Cytochem., 37(12):1845–1854 (Dec. 1989).

*Primary Examiner*—Esther L. Kepplinger
*Assistant Examiner*—Carol E. Bidwell
*Attorney, Agent, or Firm*—Nikaido, Marmelstein, Murray & Oram

[57] ABSTRACT

In order to aid in the detection of malignant diseases the sample of a body fluid is incubated with at least two receptors $R_1$ and $R_2$ in which a signal change is produced by binding of at least the receptors $R_1$ and $R_2$ to the substance to be detected in the sample solution and in which one of the two receptors contains a monoclonal antibody which binds to the amino acid sequence 311 to 335 of cytokeratin 19 and the other receptor contains a monoclonal antibody which binds to the amino acid sequence 346 to 359 of cytokeratin 19 and the signal change in the sample caused by the binding is determined.

15 Claims, No Drawings

METHOD FOR THE DETECTION OF MALIGNANT DISEASES

The invention concerns a method for the detection of malignant diseases and a suitable reagent therefor.

In clinical diagnostics the search for an indicator substance which can indicate malignant diseases has already been going on for a long time. Hopes have been placed on CEA (carcinoembryonic antigen) and TPA (tissue polypeptide antigen) as tumour markers with a broad organ specificity. Meanwhile, however, it has turned out that both proteins could not fulfill these expectations. The application of CEA has in the meantime been reduced mainly to therapeutic monitoring e.g. of colorectal carcinomas while TPA has only gained acceptance for a few indications in therapeutic monitoring because of its lack of specificity and sensitivity. Very many other proteins have been tested as indicators for malignant diseases but they were all unsatisfactory.

The cytokeratin (CK) class has also been associated with tumours. In the form of intermediary filament proteins they are components of the cytoskeleton of epithelial cells. Nineteen cytokeratins are known of which the cytokeratins 1 to 8 are denoted basic and the cytokeratins 9 to 19 acidic cytokeratins. The cytokeratins can aggregate in the cell to form tetramers. Each tetramer consists of two basic and two acidic cytokeratin molecules. Filaments are produced by the linear aggregation of tetramers. Intact cytokeratin molecules are water-insoluble as integral components of the intermediary filaments of epithelial cells. The complexity and composition of cytokeratins is different in the various epithelial tissues i.e. epithelial cells have cytokeratin compositions which are typical for the tissue. However, up to now nothing has been known about whether malignant diseases correlate with the occurrence of cytokeratins in body fluids.

It was thus the object of the present invention to provide a method with which the presence of a malignant disease can be diagnosed.

This object is achieved by a method for the detection of malignant diseases which is characterized in that the sample of a body fluid is incubated with at least two receptors $R_1$ and $R_2$ in which a signal change is produced by binding of at least one of the receptors $R_1$ and $R_2$ to the substance to be detected in the sample solution and in which one of the two receptors contains a monoclonal antibody which binds to the amino acid sequence 291 to 335 of cytokeratin 19 and the other receptor contains a monoclonal antibody which binds to the amino acid sequence 346 to 367 of cytokeratin 19 and the signal change in the sample caused by the binding is determined.

Surprisingly it was established that fragments of cytokeratin 19 are formed primarily in epithelial tumour tissues which have at most the amino acid sequence 219 to 367, but at least the sequence 311 to 359, of the complete cytokeratin 19 and have epitopes on the amino acid sequences 291 to 335 and 346 to 367 which can specifically bind to the aforementioned monoclonal antibodies or to derivatives thereof and which, in addition, can be found in body fluids. Cytokeratin 19 (CK 19) has an amino acid chain consisting of 400 amino acids. The sequence is described in Stasiak, P. C. et al., J.Invest.Dermatol. 92 (1989) 707-716, in particular on page 712 and is divided into 3 domains 1A, 1B and 2.

The fragments which are to be detected according to the present invention originate from domain 2 (helix 2). It was found that these CK 19 fragments which bind specifically to both of the above-mentioned antibodies are detectable in particular in bronchial, breast, stomach, biliary tract, liver and colon carcinomas. These fragments could not as a rule be detected in patients with inflammatory epithelial diseases of the respective tissues.

The monoclonal antibodies which are formed by the cell lines ECACC 89112803 (binds to the sequence 291 to 335, preferably to the sequence 311 to 335) and ECACC 89112804 (binds to the amino acid sequence 346 to 367, preferably to 346 to 359) are preferably used for the invention.

Other monoclonal antibodies (mAB) which bind to CK 19 but which do not bind to the CK 19 sequences defined in claim 1 are not at all suitable for the method according to the present invention or result in a reaction with insufficient clinical specificity. This is for example demonstrated by comparison studies according to Example 3 which were carried out with the mABs AE1 and b170. AE1 binds to an epitope on the amino acid sequence 153 to 219 and is described in J.Biol.Chem. 261 (1986) 4646-4654 and in J.Cell.Biol 95 (1982) 580-588. b170 binds to an epitope on the amino acid sequence 336-345, hence between the two preferred mABs of the invention and is obtainable according to Lab.Invest. 55 (1986) 497-504. The results of these experiments are shown in the following Table:

| mAB combination | malignant diseases | | benign diseases | |
| --- | --- | --- | --- | --- |
| | examined sera | positive | examined sera | positive |
| 803[1)] + 804[2)] | 24 | 11 | 24 | 4 |
| 803 + b170 | 24 | 0 | 24 | 2 |
| b170 + 804 | 24 | 4 | 24 | 1 |
| AE1 + 804 | 24 | 0 | 24 | 0 |

[1)] = ECACC 89112803
[2)] = ECACC 89112804

The test is carried out in body fluids, preferably serum. The determination is carried out according to generally known immunological methods. Very many variants are known for carrying out the intended immunological method of determination according to the present invention, all of which are suitable in this case. Thus, two or three or even more receptors can be used and incubation with the individual receptors can be carried out in different sequences in a homogeneous or heterogeneous phase. In each case the change in signal which results from the binding of at least two receptors to the fragment to be detected in the sample solution is evaluated. The variants of the methods are known to the expert and do not need to be elucidated here in more detail. The determination according to the present invention is preferably carried out either in a homogeneous phase e.g. based on an agglutination assay in which coated particles are used as receptors such as e.g. latex particles or erythrocytes which cross-link and thereby agglutinate by binding to the specifically bindable receptors and the substance to be determined, or in a heterogeneous phase, preferably as a sandwich immunoassay. In every case at least two receptors $R_1$ and $R_2$ are used of which one contains a monoclonal antibody which binds to the sequence 291 to 335 of CK 19, while the other receptor contains a monoclonal antibody which binds to the sequence 346 to 367 of CK 19. Antibodies which have an adequate epitope overlap with the antibody under consideration are also suitable. This epitope overlap can be easily detected with the aid of a competitive test system. For this purpose the extent to which an antibody competes with an antibody, which was obtained by using one or both of the aforementioned binding sequences as immunogen, for binding to a defined substrate or to a special epitope is investigated e.g. with the aid of an enzyme-immunoassay. For this a solution containing the fragment of the corresponding sequence is incubated with the defined monoclonal antibody produced according to the invention in labelled form and with an excess of the antibody under consideration. By immobilization of the complexes formed, separation of the solid from the liquid phase and detection of the bound label in one of the two phases, it is then easy to establish to what extent the monoclonal antibody under consideration can displace the defined antibody from the binding. If the displacement is at least 50% at a $10^5$-fold excess, then an epitope overlap is present and the corresponding antibody is suitable for use in the method according to the present invention.

mABs which are suitable for the invention are obtained by methods known for this purpose to one skilled in the art using CK 19 fragments which contain suitable sequences defined above or consist thereof. Complete CK 19 can also be used.

In the incubation of the body fluid with the two receptors, complexes form from $R_1$, cytokeratin 19 fragment and $R_2$. The receptors are selected such that only complexes in which $R_1$ as well as $R_2$ are bound to the cytokeratin 19 fragment generate a change in signal and thus in this way only those fragments are detected which are capable of binding to both specific antibodies.

The determination according to the present invention is preferably carried out as a sandwich immunoassay. For this receptor $R_1$ is immobilized or made to be immobilizable and reacted with the sample solution. Subsequently receptor $R_2$ is added. Complexes form from the immobilized receptor $R_1$, the CK 19 fragment to be detected and receptor $R_2$. Only complexes which are bound to the solid phase and carry a label enter into the evaluation.

In this embodiment receptor $R_1$ mediates the binding to the solid phase. For this receptor $R_1$ can either be bound directly to the solid phase or via a spacer or it can even be immobilizable. In a preferred embodiment receptor $R_1$ is a conjugate of a monoclonal antibody having the above-mentioned specificity and a specifically bindable substance. The partner capable of binding to the specifically bindable substance is bound to a solid phase. As specifically bindable pairs mention may be made of for example antigen-antibody, hapten-antibody, biotin-antibiotin-antibody, biotin-avidin, biotin-streptavidin, protein-A-immuno-γ-globulin. In this embodiment it is particularly preferably to use as $R_1$ a conjugate of the above-mentioned monoclonal antibody with biotin and a matrix which carries streptavidin on its surface as the solid phase. The immobilization of the monoclonal antibody is then effected by binding of the biotin to streptavidin. An embodiment is also preferred in which antibodies against the Fc part of the monoclonal antibody used for receptor $R_1$ or protein A molecules are bound to the surface of the solid phase whereby immobilization is then effected by binding of the Fc parts of the monoclonal antibodies of $R_1$.

In a further preferred embodiment biotin molecules are bound to a matrix and as receptor $R_1$ a conjugate of biotin and the monoclonal antibody is used. The immobilization can then be effected after carrying out the immunological reaction by addition of streptavidin.

The materials usually used in immunological methods are suitable as the solid phase. For example polymer materials as well as glass can be employed. Polystyrene, polymethacrylate, teflon, polyamide, copolymers of styrene and acrylonitrile, glass and cellulose products have proven to be especially suitable. The matrix can be present in any form e.g. as tubes, microtitre plates, beads, film, powder, particles or fibre pads. For example solid phases produced according to one of the processes described in DE-A 36 40 412 are suitable.

In this embodiment receptor $R_2$ contains in each case the other monoclonal antibody which is necessary according to the present invention. Receptor $R_2$ is labelled according to known methods. Radioactive substances, substances generating NMR signals, enzymes and fluorescent substances are suitable as the label. The detection of the label is carried out according to known methods. An enzyme is preferably employed as the label. Peroxidase, alkaline phosphatase and β-galactosidase are particularly suitable as enzymes. The enzyme is detected by addition of a substrate and measurement of the colour formed.

In the further preferred embodiment of the agglutination assay receptor $R_1$ is a particle coated with one of the two defined antibodies while the other receptor is a particle coated with the other antibody. Binding of the particle to the substance to be detected results in agglutination which can be detected by the change in turbidity.

The presence of particular fragments of cytokeratin 19 which contain two epitopes and are capable of binding to both antibodies employed can be detected with the method according to the present invention. Such fragments are formed primarily in tumour tissue.

The invention also provides a reagent for the detection of malignant diseases which is characterized in that it contains at least two receptors $R_1$ and $R_2$ in which one of the two receptors contains a monoclonal antibody which binds to the sequence 291 to 335 of cytokeratin 19 and the other receptor contains a monoclonal antibody which binds to the sequence 346 to 367 of cytokeratin 19 or an antibody capable of binding in an equivalent manner or its derivatives. The reagent preferably contains the mAB produced by the cell line ECACC 89112803 and that produced by the cell line ECACC 89112804.

The invention also provides the cell cultures ECACC 89112804 and ECACC 89112803 deposited at the European Collection of Animal Cell Cultures, Porton Down (GB) which produce antibodies against cytokeratin 19 and the antibodies themselves produced by these cell lines.

Because of their reactivity with the aforementioned epitopes of cytokeratin 19 each of the two antibodies can be used to differentiate in vivo between epitope positive and epitope negative tissues. For this the antibody or its Fab or (Fab')$_2$ fragments are bound to a label which is suitable for this purpose and conveyed to epitope positive tissue (e.g. tumours, metastases) via suitable transport media e.g. via the blood stream after injection and are bound there. The bound antibody can then be visualized using imaging techniques. Examples of labels which can be visualized are the isotopes Tc-99, I-131, I-125, In-111 for radiographic imaging and Fe, Cu, Mn, Gd or F for imaging by nuclear magnetic resonance.

By this means a method is also made possible for the diagnosis of malignant diseases in vivo in which at least one of the two receptors, which are used according to the present invention, is conveyed to body tissue and its specific binding is determined by immunoscintigraphic means.

The invention is elucidated by the following Examples.

EXAMPLE 1

Monoclonal antibody BM 19 ECACC 89112804.

Immunogen

The cytoskeleton of MCF-7 cells serves as the immunogen. The principle used for the production of these immunogens is described inter alia in Meth. in Enzymol. 134, 355 ff. (1986) and Exp. Cell Res. 173, 17 ff (1987). In summary, an extract is made from ca. $10^{10}$ MCF-7 cells using detergent-buffer (1% Triton). After centrifuging the homogenates at 2500 g the residues were extracted with saline-buffer. The insoluble fraction remaining after this extraction corresponded to the CK fraction. This fraction was used as the immunogen.

Immunization

Balb/c mice, 6 to 8 weeks old, were immunized intraperitoneally with 70 μg of the CK fraction containing CK 19 antigen in complete Freund's adjuvant. 3 further immunizations each with 70 μg antigen in incomplete Freund's adjuvant were carried out at three-month intervals.

Fusion and cloning

Spleen cells of an immunized mouse were fused with X63-Ag8-653 myeloma cells (ATCC-CRL 8375) in a 1:1 ratio according to the standard procedure according to J. of Immunol. Meth., Vol. 39, 285-308.

During the subcloning the CK specific clones were selected out by their positive reaction in immunofluorescent microscopy. Culture cells (MCF-7) as well as human tissue (liver) were used for the immunofluorescent microscopy.

Induction and Ascites 2 to $5 \times 10^6$ hybrid cells were injected intraperitoneally into mice which had been pretreated with Pristan. After 15 to 20 days ascites could be isolated with an antibody concentration of 5 to 10 mg/ml.

Specificity of the Monoclonal Antibody BM 19

The antibody has the subclass IgG2b. It reacts exclusively with CK 19 in blot analyses with CK from different tissues (e.g. epidermis, myometrium) and culture cells (e.g. MCF-7, RT 112, A 431).

EXAMPLE 2

Monoclonal antibody Ks 19.1 ECACC 89112803 (IgG2a)

Immunogen

Living cells of the human cell line MCF-7 served as immunogen.

Immunization

Balb/c mice were immunized intraperitoneally five times with ca. $10^7$ living cells.

Fusion and Cloning

An electrofusion was carried out (Eur. J. Clin. Oncol. 21, 733 ff (1985)). The plasmacytoma line X63-Ag8-653 served as the fusion partner.

Induction of Ascites 2 to $5 \times 10^6$ hybrid cells were injected intraperitoneally into mice which had been pretreated with Pristan. After 10 to 15 days ascites could be isolated with an antibody concentration of 10 to 15 mg/ml.

EXAMPLE 3

Test Procedure for CK 19

A sandwich enzyme-immunoassay was carried out to determine the CK 19 fragment in body fluids. In this procedure the monoclonal antibody Ks 19.1 (3 μg/ml) was bound for one hour at room temperature as a biotin conjugate in a volume of 100 μl PBS to the streptavidin-coated well of a microtitre plate. After washing four times with 0.05% Tween/PBS the incubation with the serum sample (2 μl serum added to 100 μl PBS) was carried out for 90 minutes at room temperature. Afterwards it is washed again four times with 0.05% Tween/PBS. Subsequently it was incubated for 90 minutes at room temperature with the monoclonal antibody BM 19 coupled to peroxidase (final concentration 250 mU/ml). After again washing four times with 0.05% Tween/PBS it was incubated at room temperature with the enzyme substrate solution ABTS® (100 mmol/l phosphate-citrate buffer pH 5.0, 1.47 mmol/l sodium perborate, 9.1 mmol/l ABTS®) and after 30 minutes the absorbance at 405 nm was measured as a measure for the analyte concentration.

The tests were carried out in the sera of patients with various diseases. The results are shown in the following table.

TABLE

| Disease | Test "Cytokeratin 19" | |
|---|---|---|
| | sera examined | positive sera |
| 1. normal sera | 19 | 0 |
| 2. benign diseases | | |
| gravidae | 20 | 2 |
| renal insufficiency | 5 | 1 |
| pancreatitis | 2 | 0 |
| cirrhosis of the liver | 5 | 3 |
| Crohn's syndrome | 5 | 0 |
| hepatitis | 5 | 3 |
| mastopathy | 1 | 0 |
| uterus myoma | 2 | 0 |
| auto-immune disease | 5 | 1 |
| prim. bil. cirrhosis | 5 | 1 |
| 3. malignant diseases | | |
| breast carcinoma | 37 | 20 |
| ovarial carcinoma | 8 | 3 |
| colon carcinoma | 7 | 7 |
| pancreatic carcinoma | 5 | 1 |
| gastric carcinoma | 5 | 3 |
| bronchial carcinoma | 9 | 4 |
| cervical carcinoma | 5 | 3 |
| prim. liver cell ca. | 5 | 4 |
| ENT carcinoma | 3 | 0 |
| biliary carcinoma | 4 | 4 |
| plasmacytoma | 5 | 0 |
| metastasing carcinoma of the scrotum | 2 | 0 |
| carcinoma of the prostate | 2 | 1 |

TABLE-continued

| | Test "Cytokeratin 19" | |
|---|---|---|
| Disease | sera examined | positive sera |
| neuroblastoma | 1 | 0 |
| colitis ulc. | 1 | 0 |

EXAMPLE 4

The overlap between the epitope of an antibody and the monoclonal antibody ECACC 89112804 was determined. The test was based on a competitive enzyme-immunoassay. For this the monoclonal antibody, e.g. ECACC 89112803 (3 μg/ml) was bound as a biotin conjugate for one hour at room temperature in a volume of 100 μl PBS (8 g/l NaCl, 0.2 g/l KCl, 1.44 g/l $NaH_2PO_4 \times 2H_2O$, 0.2 g/l $KH_2PO_4$) to the streptavidin-coated well of a microtitre plate. After washing four times with 0.05% Tween 20/PBS it was incubated for 90 minutes at room temperature with a serum sample (2 μl serum added to 100 μl PBS) with a high titre. Afterwards it was washed again four times with 0.05% Tween 20/PBS. Subsequently it was incubated simultaneously for 90 minutes at room temperature with the monoclonal antibody, e.g. ECACC 89112804 labelled with peroxidase (final concentration 250 mU/ml) and the antibody to be evaluated. After washing again four times with 0.05% Tween 20/PBS it was incubated at room temperature with the enzyme substrate solution ABTS ® (ABTS ®=2,2'-azino-di-[3-ethyl-benzthiazoline sulphonic acid(6)]-diammonium salt) and the absorbance was measured after 30 minutes at 405 nm as a measure for the analyte concentration. This value was compared with the absorbance that was obtained by incubation with the monoclonal antibody ECACC 89112804 alone. If this shows a competition of at least 50% when the antibody to be evaluated is in a $10^5$-fold excess over the monoclonal antibody ECACC 89112804-enzyme conjugate (250 mU/l) then an epitope overlap is present.

EXAMPLE 5 a) Labelling of antibodies with I-125

The antibodies described in the Examples 1 to 4 or fragments thereof were iodinated with 1 mCi I-125 according to the chloramine-T-method (Biochem.J. 89, 114–123 (1963)). Subsequently the non-reacted iodine is separated on a Sephadex G-50 column (Pharmacia) and the immunoreactivity of the monoclonal antibody was checked in an ELISA.

b) Localization of tumours with monoclonal antibody labelled with iodine

Naked mice (Balb/c nu/nu) are inoculated subcutaneously with $3-5 \times 10^{10}$ HeLa cells (type 2). After ca. 8 weeks those mice which had formed a solid tumour were injected with 200 μl KI (potassium iodide) (1 mg/ml) in PBS (phosphate-buffered saline). 24 h after the KI injection ca. 50 μg of the labelled monoclonal antibody or 70 μg of the corresponding antibody fragment are injected. The distribution of the radioactivity is observed over 20 days with the aid of an autoradiographic instrument (e.g. from General Electric). An accumulation of the radioactivity can be observed in the region of the solid tumour as a result of the specific binding to both monoclonal antibodies.

Details of the deposit of the two aforementioned cell lines are shown in the following.

We claim:

1. Reagent to aid in the detection of malignant diseases, comprising at least two receptors R1 and R2, wherein one of the receptors contains a monoclonal antibody which specifically binds to the sequence 311 to 335 of cytokeratin 19 and other receptor contains a monoclonal antibody which specifically binds to the sequence 346 to 359 of cytokeratin 19.

2. Reagent according to claim 1, wherein receptor R1 is a biotin conjugate of a monoclonal antibody which specifically binds to amino acid sequence 311 or 346 to 359 of cytokeratin 19 and can be bound to a solid phase which is coated with streptavidin.

3. Reagent according to claim 2, wherein said reagent contains the antibody which specifically binds to the sequence 311 to 335 of cytokeratin 19 produced by the cell line ECACC 89112803 or is an antibody which binds to the same epitope as the antibody produced by the cell line ECACC 89112803.

4. Reagent according to claim 2, wherein said reagent contains the antibody which specifically binds to the sequence 346 to 359 of cytokeratin 19 produced by the cell line ECACC 89112804 or is an antibody which binds to the same epitope as the antibody produced by the cell line ECACC 89112804.

5. The monoclonal antibody produced by the cell line ECACC 89112803.

6. The monoclonal antibody produced by the cell line ECACC 89112804.

7. Cell line ECACC 89112803.

8. Cell line ECACC 89112804.

9. Method for screening for malignant diseases, comprising the steps of:
incubating a sample of a body fluid with at least two receptors R1 and R2 in a liquid phase, wherein one of the two receptors contains a monoclonal antibody which specifically binds to the amino acid sequence 311 to 335 of cytokeratin 19 and the other receptor contains a monoclonal antibody which specifically binds to the amino acid sequence 346 to 359 of cytokeratin 19, to produce a signal change by binding of the receptors R1 and R2 to the substance to be detected in the sample solution, and
detecting the signal change in the sample caused by the binding as an indication of the presence of a malignant disease.

10. The method according to claim 9, wherein the antibody specifically binding to the sequence 311 to 335 is produced by the cell line ECACC 89112803 or is an antibody which specifically binds to the same epitope as the antibody produced by the line ECACC 89112803.

11. The method according to claim 9, wherein the antibody specifically binding to the sequence 346 to 359 is produced by the cell line ECACC 89112804 or is an antibody which specifically binds to the same epitope as the antibody produced by the cell line ECACC 89112804.

12. Method according to claim 9, wherein R1 is bound to a solid phase and R2 is detectably labelled.

13. The method according to claim 12 further comprising separating said solid phase from said liquid phase and detecting R2 in one of the two phases.

14. The method according to claim 13, wherein said solid phase is coated with streptavidin and receptor R1 is a biotin conjugate of one of said two antibodies, and the binding of R1 to the solid phase is effected by the binding of biotin to streptavidin.

15. The method according to claim 12, wherein R2 is labelled with a radioactive isotope, with an enzyme, or with a substance which generates fluorescent or NMR signals.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1394 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 33..1232

( x i ) SEQUENCE DESCRIPTION: SEQ ID NO:1:

```
CGGGGGTTGC TCCGTCCGTG CTCCGCCTCG CC ATG ACT TCC TAC AGC TAT CGC      53
                                     Met Thr Ser Tyr Ser Tyr Arg
                                      1               5

CAG TCG TCG GCC ACG TCG TCC TTC GGA GGC CTG GGC GGC GGC TCC GTG    101
Gln Ser Ser Ala Thr Ser Ser Phe Gly Gly Leu Gly Gly Gly Ser Val
         10                  15                  20

CGT TTT GGG CCG GGG GTG GCT TTT CGC GCG CCC AGC ATT CAC GGG GGC    149
Arg Phe Gly Pro Gly Val Ala Phe Arg Ala Pro Ser Ile His Gly Gly
     25                  30                  35

TCC GGC GGC CGC GGC GTA TCC GTG TCC TCC GCC CGC TTT GTG TCC TCG    197
Ser Gly Gly Arg Gly Val Ser Val Ser Ser Ala Arg Phe Val Ser Ser
 40                  45                  50                  55
```

| | | | | | | | | | | | | | | | | |
|---|---|---|---|---|---|---|---|---|---|---|---|---|---|---|---|---|
|TCC|TCC|TCG|GGG|GGC|TAC|GGC|GGC|GGC|TAC|GGC|GGC|GTC|CTG|ACC|GCG|245|
|Ser|Ser|Ser|Gly|Gly|Tyr|Gly|Gly|Gly|Tyr|Gly|Gly|Val|Leu|Thr|Ala| |
| | | |60| | | |65| | | | |70| | | | |

| | | | | | | | | | | | | | | | | |
|---|---|---|---|---|---|---|---|---|---|---|---|---|---|---|---|---|
|TCC|GAC|GGG|CTG|CTG|GCG|GGC|AAC|GAG|AAG|CTA|ACC|ATG|CAG|AAC|CTC|293|
|Ser|Asp|Gly|Leu|Leu|Ala|Gly|Asn|Glu|Lys|Leu|Thr|Met|Gln|Asn|Leu| |
| | |75| | | | |80| | | | |85| | | | |

| | | | | | | | | | | | | | | | | |
|---|---|---|---|---|---|---|---|---|---|---|---|---|---|---|---|---|
|AAC|GAC|CGC|CTG|GCC|TCC|TAC|CTG|GAC|AAG|GTG|CGC|GCC|CTG|GAG|GCG|341|
|Asn|Asp|Arg|Leu|Ala|Ser|Tyr|Leu|Asp|Lys|Val|Arg|Ala|Leu|Glu|Ala| |
| | |90| | | | |95| | | | |100| | | | |

| | | | | | | | | | | | | | | | | |
|---|---|---|---|---|---|---|---|---|---|---|---|---|---|---|---|---|
|GCC|AAC|GGC|GAG|CTA|GAG|GTG|AAG|ATC|CGC|GAC|TGG|TAC|CAG|AAG|CAG|389|
|Ala|Asn|Gly|Glu|Leu|Glu|Val|Lys|Ile|Arg|Asp|Trp|Tyr|Gln|Lys|Gln| |
| |105| | | | |110| | | | |115| | | | | |

| | | | | | | | | | | | | | | | | |
|---|---|---|---|---|---|---|---|---|---|---|---|---|---|---|---|---|
|GGG|CCT|GGG|CCC|TCC|CGC|GAC|TAC|AGC|CAC|TAC|TAC|ACG|ACC|ATC|CAG|437|
|Gly|Pro|Gly|Pro|Ser|Arg|Asp|Tyr|Ser|His|Tyr|Tyr|Thr|Thr|Ile|Gln| |
|120| | | | |125| | | | |130| | | | |135| |

| | | | | | | | | | | | | | | | | |
|---|---|---|---|---|---|---|---|---|---|---|---|---|---|---|---|---|
|GAC|CTG|CGG|GAC|AAG|ATT|CTT|GGT|GCC|ACC|ATT|GAG|AAC|TCC|AGG|ATT|485|
|Asp|Leu|Arg|Asp|Lys|Ile|Leu|Gly|Ala|Thr|Ile|Glu|Asn|Ser|Arg|Ile| |
| | | |140| | | | |145| | | | |150| | | |

| | | | | | | | | | | | | | | | | |
|---|---|---|---|---|---|---|---|---|---|---|---|---|---|---|---|---|
|GTC|CTG|CAG|ATC|GAC|AAC|GCC|CGT|CTG|GCT|GCA|GAT|GAC|TTC|CGA|ACC|533|
|Val|Leu|Gln|Ile|Asp|Asn|Ala|Arg|Leu|Ala|Ala|Asp|Asp|Phe|Arg|Thr| |
| | | | |155| | | | |160| | | | |165| | |

| | | | | | | | | | | | | | | | | |
|---|---|---|---|---|---|---|---|---|---|---|---|---|---|---|---|---|
|AAG|TTT|GAG|ACG|GAA|CAG|GCT|CTG|CGC|ATG|AGC|GTG|GAG|GCC|GAC|ATC|581|
|Lys|Phe|Glu|Thr|Glu|Gln|Ala|Leu|Arg|Met|Ser|Val|Glu|Ala|Asp|Ile| |
| | | |170| | | | |175| | | | |180| | | |

| | | | | | | | | | | | | | | | | |
|---|---|---|---|---|---|---|---|---|---|---|---|---|---|---|---|---|
|AAC|GGC|CTG|CGC|AGG|GTG|CTG|GAT|GAG|CTG|ACC|CTG|GCC|AGG|ACC|GAC|629|
|Asn|Gly|Leu|Arg|Arg|Val|Leu|Asp|Glu|Leu|Thr|Leu|Ala|Arg|Thr|Asp| |
| |185| | | | |190| | | | |195| | | | | |

| | | | | | | | | | | | | | | | | |
|---|---|---|---|---|---|---|---|---|---|---|---|---|---|---|---|---|
|CTG|GAG|ATG|CAG|ATC|GAA|GGC|CTC|AAG|GAA|GAG|CTG|GCC|TAC|CTG|AAG|677|
|Leu|Glu|Met|Gln|Ile|Glu|Gly|Leu|Lys|Glu|Glu|Leu|Ala|Tyr|Leu|Lys| |
|200| | | | |205| | | | |210| | | | |215| |

| | | | | | | | | | | | | | | | | |
|---|---|---|---|---|---|---|---|---|---|---|---|---|---|---|---|---|
|AAG|AAC|CAT|GAG|GAG|GAA|ATC|AGT|ACG|CTG|AGG|GGC|CAA|GTG|GGA|GGC|725|
|Lys|Asn|His|Glu|Glu|Glu|Ile|Ser|Thr|Leu|Arg|Gly|Gln|Val|Gly|Gly| |
| | | |220| | | | |225| | | | |230| | | |

| | | | | | | | | | | | | | | | | |
|---|---|---|---|---|---|---|---|---|---|---|---|---|---|---|---|---|
|CAG|GTG|AGT|GTG|GAG|GTG|GAT|TCC|GCT|CCG|GGC|ACC|GAT|CTC|GCC|AAG|773|
|Gln|Val|Ser|Val|Glu|Val|Asp|Ser|Ala|Pro|Gly|Thr|Asp|Leu|Ala|Lys| |
| | |235| | | | |240| | | | |245| | | | |

| | | | | | | | | | | | | | | | | |
|---|---|---|---|---|---|---|---|---|---|---|---|---|---|---|---|---|
|ATC|CTG|AGT|GAC|ATG|CGA|AGC|CAA|TAT|GAG|GTG|ATG|GCC|GAG|CAG|AAC|821|
|Ile|Leu|Ser|Asp|Met|Arg|Ser|Gln|Tyr|Glu|Val|Met|Ala|Glu|Gln|Asn| |
| | |250| | | | |255| | | | |260| | | | |

| | | | | | | | | | | | | | | | | |
|---|---|---|---|---|---|---|---|---|---|---|---|---|---|---|---|---|
|CGG|AAG|GAT|GCT|GAA|GCC|TGG|TTC|ACC|AGC|CGG|ACT|GAA|GAA|TTG|AAC|869|
|Arg|Lys|Asp|Ala|Glu|Ala|Trp|Phe|Thr|Ser|Arg|Thr|Glu|Glu|Leu|Asn| |
|265| | | | |270| | | | |275| | | | | | |

| | | | | | | | | | | | | | | | | |
|---|---|---|---|---|---|---|---|---|---|---|---|---|---|---|---|---|
|CGG|GAG|GTC|GCT|GGC|CAC|ACG|GAG|CAG|CTC|CAG|ATG|AGC|AGG|TCC|GAG|917|
|Arg|Glu|Val|Ala|Gly|His|Thr|Glu|Gln|Leu|Gln|Met|Ser|Arg|Ser|Glu| |
|280| | | | |285| | | | |290| | | | |295| |

| | | | | | | | | | | | | | | | | |
|---|---|---|---|---|---|---|---|---|---|---|---|---|---|---|---|---|
|GTT|ACT|GAC|CTG|CGG|CGC|ACC|CTT|CAG|GGT|CTT|GAG|ATT|GAG|CTG|CAG|965|
|Val|Thr|Asp|Leu|Arg|Arg|Thr|Leu|Gln|Gly|Leu|Glu|Ile|Glu|Leu|Gln| |
| | | | |300| | | | |305| | | | |310| | |

| | | | | | | | | | | | | | | | | |
|---|---|---|---|---|---|---|---|---|---|---|---|---|---|---|---|---|
|TCA|CAG|CTG|AGC|ATG|AAA|GCT|GCC|TTG|GAA|GAC|ACA|CTG|GCA|GAA|ACG|1013|
|Ser|Gln|Leu|Ser|Met|Lys|Ala|Ala|Leu|Glu|Asp|Thr|Leu|Ala|Glu|Thr| |
| | | |315| | | | |320| | | | |325| | | |

| | | | | | | | | | | | | | | | | |
|---|---|---|---|---|---|---|---|---|---|---|---|---|---|---|---|---|
|GAG|GCG|CGC|TTT|GGA|GCC|CAG|CTG|GCG|CAT|ATC|CAG|GCG|CTG|ATC|AGC|1061|
|Glu|Ala|Arg|Phe|Gly|Ala|Gln|Leu|Ala|His|Ile|Gln|Ala|Leu|Ile|Ser| |
| | |330| | | | |335| | | | |340| | | | |

| | | | | | | | | | | | | | | | | |
|---|---|---|---|---|---|---|---|---|---|---|---|---|---|---|---|---|
|GGT|ATT|GAA|GCC|CAG|CTG|GCG|GAT|GTG|CGA|GCT|GAT|AGT|GAG|CGG|CAG|1109|
|Gly|Ile|Glu|Ala|Gln|Leu|Ala|Asp|Val|Arg|Ala|Asp|Ser|Glu|Arg|Gln| |
| |345| | | | |350| | | | |355| | | | | |

| | | | | | | | | | | | | | | | | |
|---|---|---|---|---|---|---|---|---|---|---|---|---|---|---|---|---|
|AAT|CAG|GAG|TAC|CAG|CGG|CTC|ATG|GAC|ATC|AAG|TCG|CGG|CTG|GAG|CAG|1157|
|Asn|Gln|Glu|Tyr|Gln|Arg|Leu|Met|Asp|Ile|Lys|Ser|Arg|Leu|Glu|Gln| |
|360| | | | |365| | | | |370| | | | |375| |

| | | | | | | | | | | | | | | | | |
|---|---|---|---|---|---|---|---|---|---|---|---|---|---|---|---|---|
|GAG|ATT|GCC|ACC|TAC|CGC|AGC|CTG|CTC|GAG|GGA|CAG|GAA|GAT|CAC|TAC|1205|

```
Glu  Ile  Ala  Thr  Tyr  Arg  Ser  Leu  Leu  Glu  Gly  Gln  Glu  Asp  His  Tyr
              380                      385                      390

AAC  AAT  TTG  TCT  GCC  TCC  AAG  GTC  CTC  TGAGGCAGCA  GGCTCTGGGG                1252
Asn  Asn  Leu  Ser  Ala  Ser  Lys  Val  Leu
              395                      400

CTTCTGCTGT  CCTTTGGAGG  GTGTCTTCTG  GGTAGAGGGA  TGGGAAGGAA  GGGACCCTTA             1312

CCCCCGGCTC  TTCTCCTGAC  CTGCCAATAA  AAATTTATGG  TCCAAGGGAA  AAAAAAAAA              1372

AAAAAAAAAA  AAAAAAAAAA  AA                                                        1394
```

( 2 ) INFORMATION FOR SEQ ID NO:2:

( i ) SEQUENCE CHARACTERISTICS:
        ( A ) LENGTH: 400 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Ser  Tyr  Ser  Tyr  Arg  Gln  Ser  Ser  Ala  Thr  Ser  Ser  Phe  Gly
 1                   5                    10                        15

Gly  Leu  Gly  Gly  Gly  Ser  Val  Arg  Phe  Gly  Pro  Gly  Val  Ala  Phe  Arg
              20                        25                   30

Ala  Pro  Ser  Ile  His  Gly  Gly  Ser  Gly  Gly  Arg  Gly  Val  Ser  Val  Ser
              35                        40                        45

Ser  Ala  Arg  Phe  Val  Ser  Ser  Ser  Ser  Gly  Gly  Tyr  Gly  Gly  Gly
 50                        55                        60

Tyr  Gly  Gly  Val  Leu  Thr  Ala  Ser  Asp  Gly  Leu  Leu  Ala  Gly  Asn  Glu
 65                        70                        75                        80

Lys  Leu  Thr  Met  Gln  Asn  Leu  Asn  Asp  Arg  Leu  Ala  Ser  Tyr  Leu  Asp
                        85                        90                        95

Lys  Val  Arg  Ala  Leu  Glu  Ala  Ala  Asn  Gly  Glu  Leu  Glu  Val  Lys  Ile
                  100                      105                      110

Arg  Asp  Trp  Tyr  Gln  Lys  Gln  Gly  Pro  Gly  Pro  Ser  Arg  Asp  Tyr  Ser
                  115                      120                      125

His  Tyr  Tyr  Thr  Thr  Ile  Gln  Asp  Leu  Arg  Asp  Lys  Ile  Leu  Gly  Ala
                  130                      135                      140

Thr  Ile  Glu  Asn  Ser  Arg  Ile  Val  Leu  Gln  Ile  Asp  Asn  Ala  Arg  Leu
145                      150                      155                      160

Ala  Ala  Asp  Asp  Phe  Arg  Thr  Lys  Phe  Glu  Thr  Glu  Gln  Ala  Leu  Arg
                  165                      170                      175

Met  Ser  Val  Glu  Ala  Asp  Ile  Asn  Gly  Leu  Arg  Arg  Val  Leu  Asp  Glu
                  180                      185                      190

Leu  Thr  Leu  Ala  Arg  Thr  Asp  Leu  Glu  Met  Gln  Ile  Glu  Gly  Leu  Lys
                  195                      200                      205

Glu  Glu  Leu  Ala  Tyr  Leu  Lys  Lys  Asn  His  Glu  Glu  Glu  Ile  Ser  Thr
 210                      215                      220

Leu  Arg  Gly  Gln  Val  Gly  Gly  Gln  Val  Ser  Val  Glu  Val  Asp  Ser  Ala
 225                      230                      235                      240

Pro  Gly  Thr  Asp  Leu  Ala  Lys  Ile  Leu  Ser  Asp  Met  Arg  Ser  Gln  Tyr
                  245                      250                      255

Glu  Leu  Met  Ala  Glu  Gln  Asn  Arg  Lys  Asp  Ala  Glu  Ala  Trp  Phe  Thr
                  260                      265                      270

Ser  Arg  Thr  Glu  Glu  Leu  Asn  Arg  Glu  Val  Ala  Gly  His  Thr  Glu  Gln
                  275                      280                      285

Leu  Gln  Met  Ser  Arg  Ser  Glu  Val  Thr  Asp  Leu  Arg  Arg  Thr  Leu  Gln
                  290                      295                      300
```

```
Gly Leu Glu Ile Glu Leu Gln Ser Gln Leu Ser Met Lys Ala Ala Leu
305             310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Ala Asp Val
                340                 345                 350

Arg Ala Asp Ser Glu Arg Gln Asn Gln Glu Tyr Gln Arg Leu Met Asp
            355                 360                 365

Ile Lys Ser Arg Leu Glu Gln Glu Ile Ala Thr Tyr Arg Ser Leu Leu
    370                 375                 380

Glu Gly Gln Glu Asp His Tyr Asn Asn Leu Ser Ala Ser Lys Val Leu
385                 390                 395                 400
```